(12) United States Patent
Selvaggi

(10) Patent No.: US 12,394,505 B2
(45) Date of Patent: Aug. 19, 2025

(54) ELECTRONIC HEALTH RECORD INTEROPERABILITY TOOL

(71) Applicant: Richard R. Selvaggi, Commerce, TX (US)

(72) Inventor: Richard R. Selvaggi, Commerce, TX (US)

( * ) Notice: Subject to any disclaimer, the term of this patent is extended or adjusted under 35 U.S.C. 154(b) by 466 days.

(21) Appl. No.: 17/674,323

(22) Filed: Feb. 17, 2022

(65) Prior Publication Data

US 2022/0172808 A1 Jun. 2, 2022

Related U.S. Application Data

(63) Continuation-in-part of application No. 16/406,907, filed on May 8, 2019, now abandoned.

(Continued)

(51) Int. Cl.
| | | |
|---|---|---|
| G16H 10/60 | (2018.01) | |
| G06F 3/06 | (2006.01) | |
| G06F 16/16 | (2019.01) | |

(52) U.S. Cl.
CPC .......... *G16H 10/60* (2018.01); *G06F 3/0643* (2013.01); *G06F 16/164* (2019.01)

(58) Field of Classification Search
None
See application file for complete search history.

(56) References Cited

U.S. PATENT DOCUMENTS 7,194,479 B1 * 3/2007 Packham ............ G06F 11/3684
717/124
8,600,776 B2 12/2013 Raduchel (Continued)

FOREIGN PATENT DOCUMENTS

| CA | 2942566 A1 | 9/2015 | | |
|---|---|---|---|---|
| WO | WO-2017100352 A1 | * | 6/2017 | ............ G06F 16/86 |
| WO | WO-2018089875 A2 | * | 5/2018 | ............ G16H 10/60 |

OTHER PUBLICATIONS

Ong TC, Kahn MG, Kwan BM, Yamashita T, Brandt E, Hosokawa P, Uhrich C, Schilling LM. Dynamic-ETL: a hybrid approach for health data extraction, transformation and loading. BMC Med Inform Decis Mak. Sep. 1, 2017;17(1):134. doi: 10.1186/s12911-017-0532-3. PMID: 28903729; PMCID: PMC5598056. (Year: 2017).*

(Continued)

*Primary Examiner* — Christopher L Gilligan
*Assistant Examiner* — Jessica Marie Webb
(74) *Attorney, Agent, or Firm* — James H. Ortega; David W. Carstens; Carstens, Allen & Gourley, LLP

(57) ABSTRACT

Disclosed principles permit exchange of patient information between disparate Electronic Health Record (EHR) systems by identifying a source standard medical record (SMR), breaking the SMR into elemental record parts without data or patient information, labeling each SMR elemental part with a Field Indicator Code (FIC), and concatenating the FIC labeled elemental parts. The concatenated FIC labeled elemental parts are used as a guide by disparate EHR systems to break down their EHRs into the same electronic elemental parts, labeling the corresponding elemental parts with the appropriate FIC, and then concatenating each part. As data is entered into an EHR during a patient service, a unique Accountability Information (A-I) label is created for that service and added to the FIC as data is added to the corresponding elemental part. An importing EHR system reads the standard FICs and places each A-I+FIC elemental part with data into its matching standardized FIC label elemental part where the data may be read.

16 Claims, 5 Drawing Sheets

Structured elemental parts are selected, saved, cut, and exported as unstructured elemental parts.

Related U.S. Application Data

(60) Provisional application No. 62/668,449, filed on May 8, 2018.

(56) References Cited

U.S. PATENT DOCUMENTS

| | | | |
|---|---|---|---|
| 9,202,084 | B2 | 12/2015 | Moore |
| 9,678,956 | B2 | 6/2017 | Bell |
| 9,820,658 | B2 | 11/2017 | Tran |
| 10,468,126 | B1 | 11/2019 | Harding et al. |
| 2009/0080408 | A1* | 3/2009 | Natoli ............... H04L 67/565 370/351 |
| 2010/0146013 | A1 | 6/2010 | Mather |
| 2011/0246224 | A1 | 10/2011 | Green et al. |
| 2012/0303388 | A1 | 11/2012 | Vishnubhatla et al. |
| 2013/0159021 | A1 | 6/2013 | Felsher |
| 2013/0197938 | A1 | 8/2013 | Bayouk et al. |
| 2013/0218917 | A1* | 8/2013 | Bell ..................... G06F 16/93 707/756 |
| 2014/0039931 | A1 | 2/2014 | Joe et al. |
| 2014/0136234 | A1 | 5/2014 | Weinstein |
| 2014/0223277 | A1* | 8/2014 | Kimber ............ G06F 40/174 715/223 |
| 2015/0100578 | A1 | 4/2015 | Rosen et al. |
| 2015/0213222 | A1 | 7/2015 | Amarasingham et al. |
| 2016/0019299 | A1 | 1/2016 | Boloor et al. |
| 2016/0085914 | A1 | 3/2016 | Douglass et al. |
| 2016/0210427 | A1* | 7/2016 | Mynhier ............... G16H 10/60 |
| 2017/0235890 | A1* | 8/2017 | Chen ................ G06Q 10/00 705/3 |
| 2018/0032573 | A1 | 2/2018 | Jarman et al. |
| 2018/0165416 | A1 | 6/2018 | Saxena et al. |
| 2018/0330801 | A1 | 11/2018 | Malaviya et al. |

OTHER PUBLICATIONS (N.a.), "Health Level 7", 2017, Wikipedia, retrieved via Wayback Machine, all pages, https://web.archive.org/web/20170724080407/ https://en.wikipedia.org/wiki/Health_Level_7 (Year: 2017).*

Dolin RH, Alschuler L, Beebe C, Biron PV, Boyer SL, Essin D, Kimber E, Lincoln T, Mattison JE. The HL7 Clinical Document Architecture. J Am Med Inform Assoc. Nov.-Dec. 2001;8(6):552-69. doi: 10.1136/jamia.2001.0080552. PMID: 11687563; PMCID: PMC130066. (Year: 2001).*

Kernan, Rich, "Clinical Document Architecture (CDA), Consolidated-CDA (C-CDA) and their Role in Meaningful Use (MU)", 2012, National Coordinator for Health Information Technology (ONC), all pages, https://www.healthit.gov/sites/default/files/resources/cda_c-cda_theirrole_in_mu.pdf (Year: 2012).*

Ross et al, "The HMO Research Network Virtual Data Warehouse: A Public Data Model to Support Collaboration", EDM Forum Community, The Berkeley Electronic Press, Mar. 24, 2014.

* cited by examiner

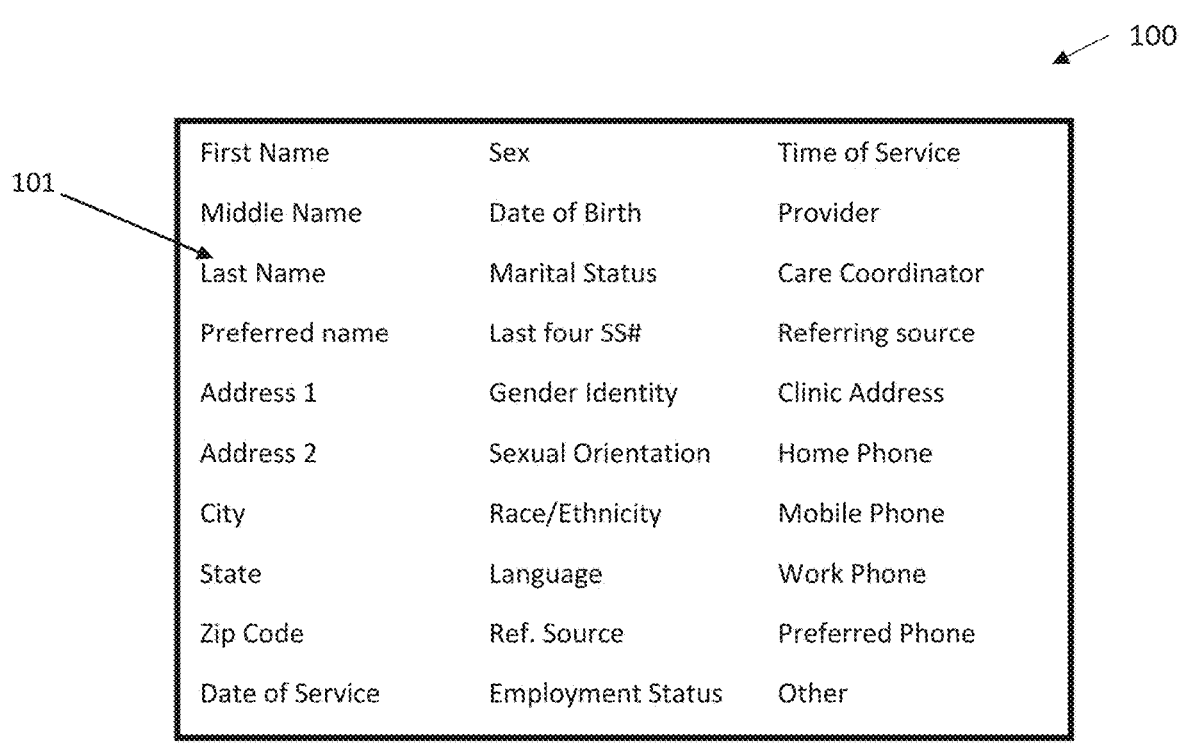
FIG. 1 Source Standard Medical Record FIC Labeled Elemental Parts

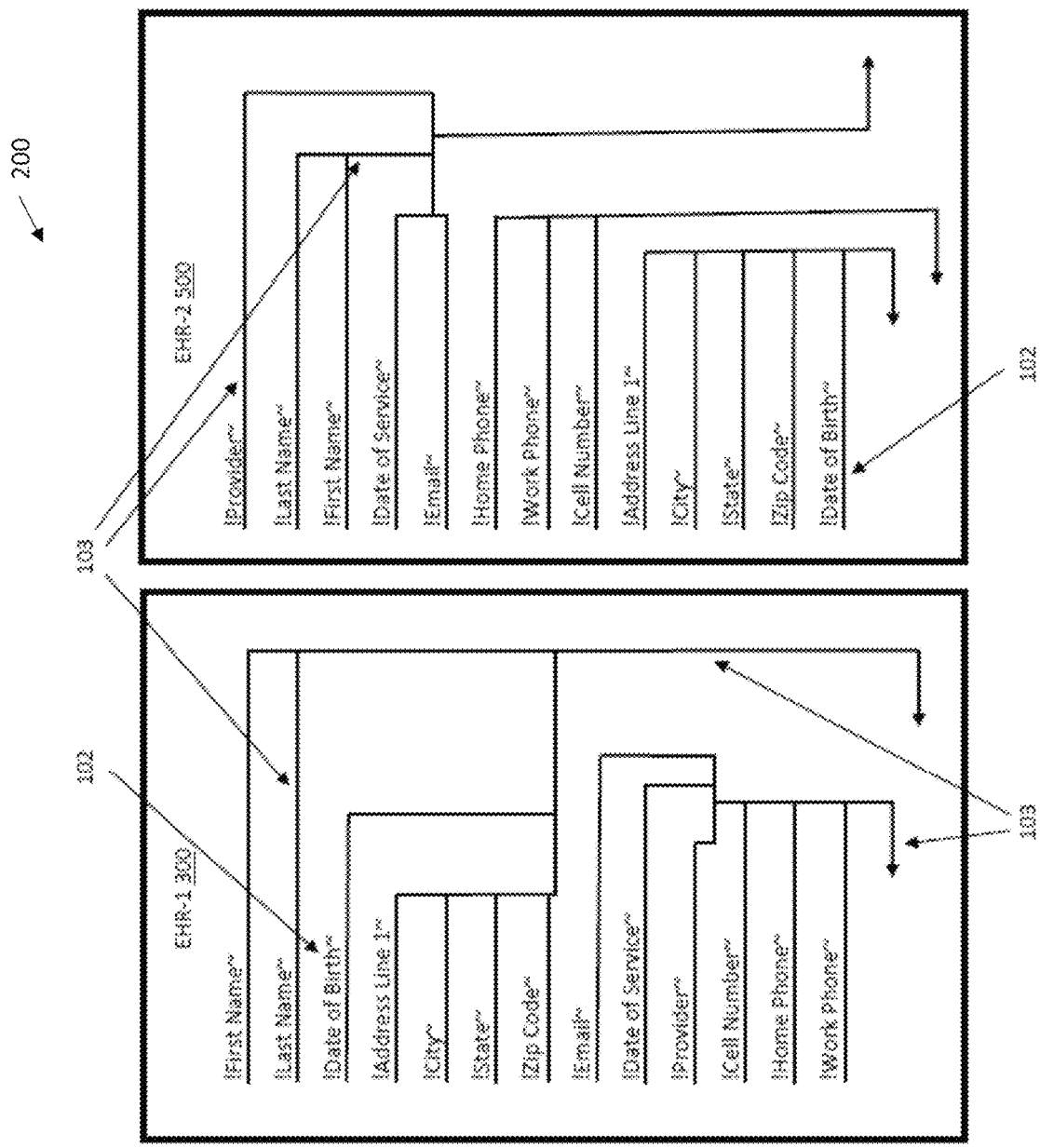
FIG. 2 Structured FIC standard electronic elemental parts

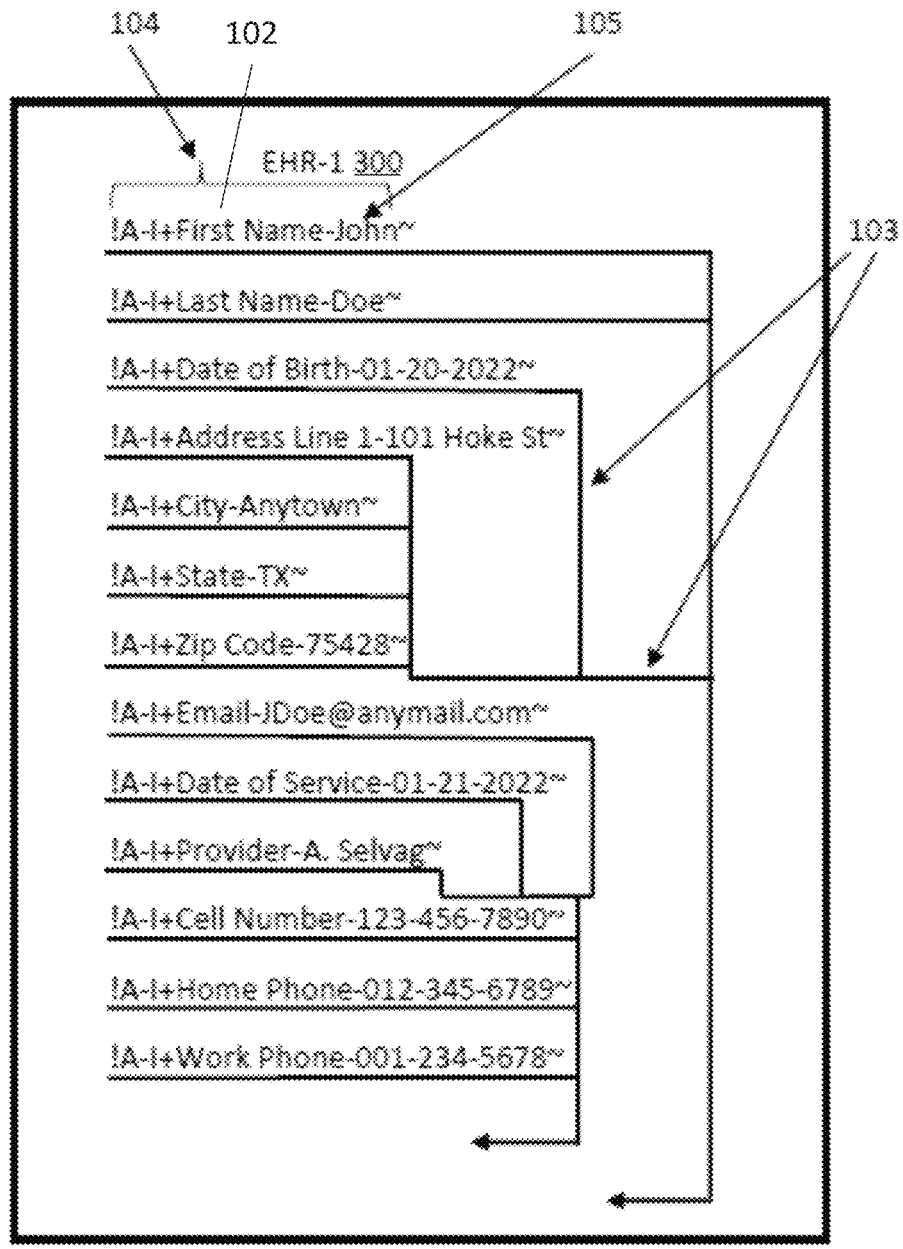
FIG. 3 Structured A-I + FIC standard elemental parts with data

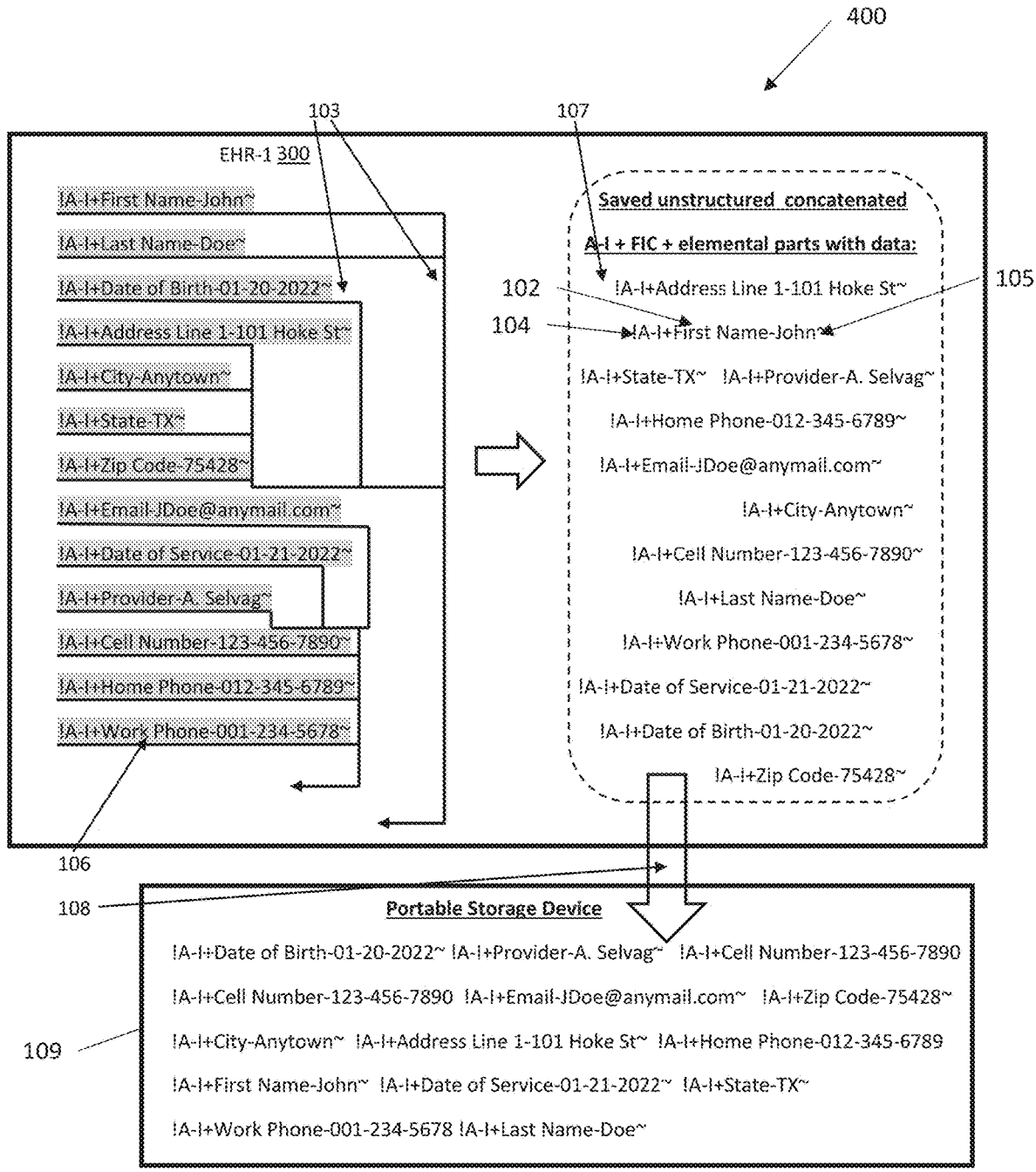
FIG. 4 - Structured elemental parts are selected, saved, cut, and exported as unstructured elemental parts.

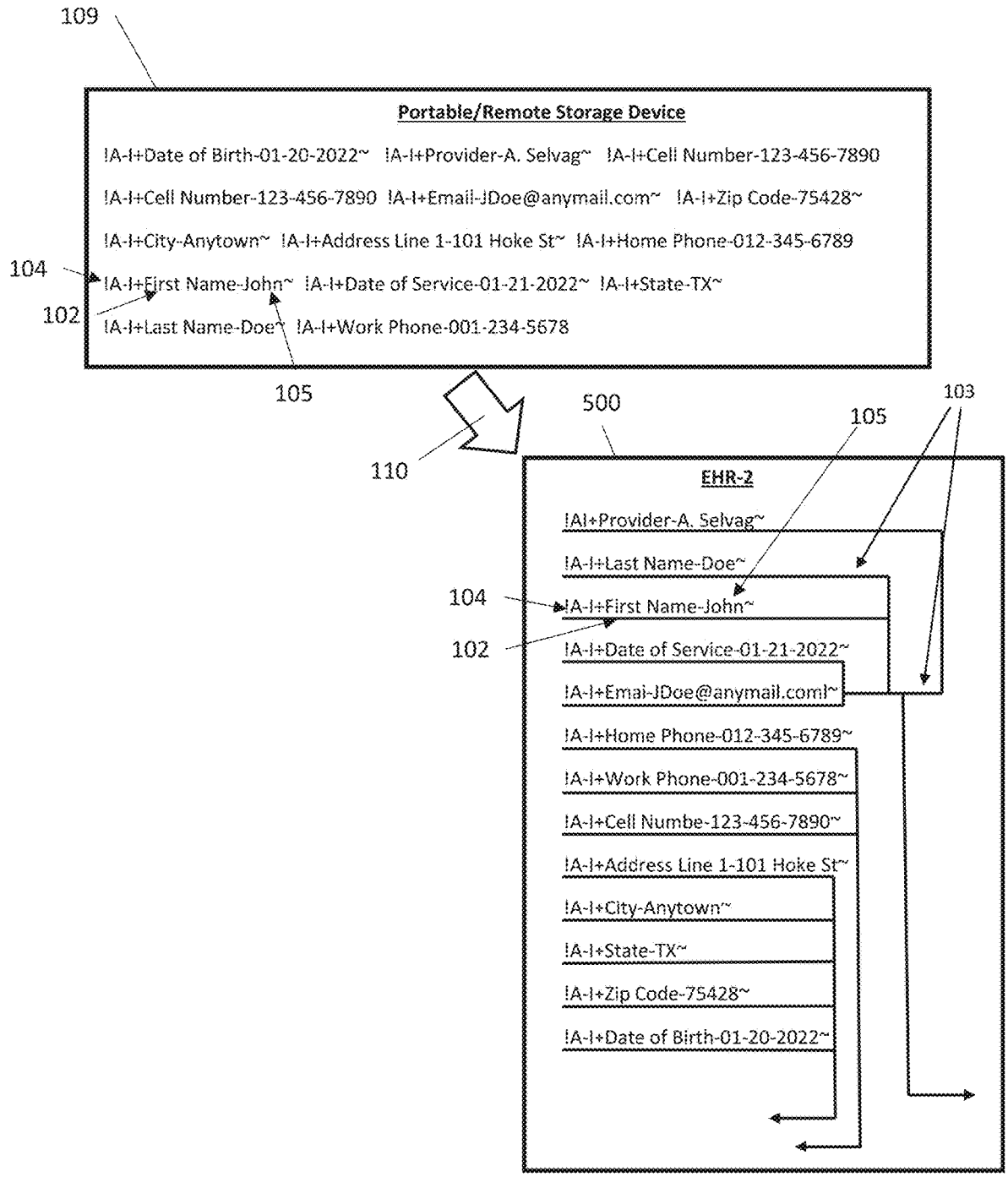
FIG. 5 - Unstructured elemental data import, FIC matching, and insertion into EHR-2's structure.

ELECTRONIC HEALTH RECORD INTEROPERABILITY TOOL

RELATED APPLICATION

The present disclosure is a continuation-in-part application of U.S. Non-Provisional patent application Ser. No. 16/406,907, filed May 8, 2019, which claims priority to and is a non-provisional conversion of U.S. Provisional Patent Application No. 62/668,449, filed May 8, 2018, which is incorporated herein by reference in its entirety for all purposes.

TECHNICAL FIELD

The present disclosure relates to electronic health records, and in particular to systems and methods for providing interoperability between differently structured or formatted electronic health records.

BACKGROUND

Current medical practices keep records of patient data by recording information about patients and corresponding medical events in a Standard Medical Record (SMR). A SMR may be paper-based, it could be stored electronically locally, stored electronically at a central location, or stored electronically in the cloud. Formats of SMR's can vary, but the kinds of medical information contained within different SMR's are of the same type. For example, there can be basic information to identify each patient, as well as records indicating the patient's blood pressure and other test results.

The vast majority of SMR's are migrating from paper-based records to Electronic Health Records (EHR's). The SMR is the basis for the information found in all paper and electronic EHRs. Patient information in every EHR is organized into the same categories as in a paper-based SMR. Depending on the needs of the health practice, each health record will have more extensive portions of the SMR, while other portions may be entirely eliminated. Although different health records use similar or the same SMR designs, the terminology and organization utilized will vary. The electronic data configuration and structure of similar standard medical record information is different for each EHR system format, making sharing of electronic information difficult and impractical among all the various EHR formats available in the marketplace. Differences in structures between paper-based SMRs do not result in a problem when sharing medical records since this requires human interaction to interpret the contents of such SMRs. However, differences in the structural formats of EHRs pose a problem for the sharing of such EHRs since translation software is needed to convert the contents of one format type of EHR into an EHR formatted for a different system.

In order to increase efficiency and comply with new requirements to convert to EHR's, the vast majority of medical practices are entering all patient data electronically into their own unique EHR systems. These EHR systems are being developed by various companies who design their products to meet the individual needs of various medical organizations. The EHR's work well within the organizations who use the same EHR software systems, but cannot be readily shared with EHR's in systems independently developed by other companies. This inability to share electronic information can also occur for different EHRs within the same EHR company. This form of incompatibility results in not being able to share electronic medical records between different medical organizations that are used by the patient when those organizations use different EHR systems. For example, a patient may be travelling when in need of medical attention, and while the patient's records may be accessible remotely at the travel site, the format of the medical data will likely be incompatible if different EHR systems are involved.

With the increasing development and use of EHR systems, there is need in the art for a way of sharing medical records to be able to efficiently and accurately transfer a patient's medical information electronically. However, as of the filing of this disclosure, there are no practical universal EHR interoperability tools available, nor are there any known future tools proposed that will provide a universal workable solution. A key problem is that there are literally hundreds of EHR products available with different technology architectures, file formats, service models, and capabilities. Consequently, the electronic data storage configuration of similar standard medical record information is generally different for each EHR system, making sharing of electronic information difficult and impractical.

One way of solving this problem is to create custom software to convert EHR's from one format directly to a format used by a different system. While this type of "transcoding" could be a workable solution for interoperability, it would only be useful between two specific systems for which the transcoding software has been created. In addition, the high cost of developing data interchange transcoding software that exchanges medical records directly between disparate EHR systems results in a lack of incentive to develop interoperability. Additionally, there is no standard for storing electronic medical records on a portable device in a way that enables sharing medical records between disparate EHR systems.

A preferred solution for interoperability between disparate EHR systems would be to devise a universal standard for an intermediate EHR file format, thus allowing software developers to create data interchange software to import and export EHR data using a standardized intermediate data interchange format. Once such interchange software is created for a particular EHR system, it would allow sharing of patient records with any other EHR system which can import and export patient records in the standardized data interchange format.

One current effort for creating an intermediate EHR is to translate portions of the EHR into a standardized format, such as the draft standard called Fast Healthcare Interoperability Resources (FHIR), proposed by Health Level Seven International. Upon request, the stored intermediate EHR is translated into a third format needed by a different disparate EHR. However, the resulting intermediate EHR file structure was complex and expensive to implement. Modifying software for existing EHR systems to export and import these complex files was a considerable effort and cost. Individual practitioners and small healthcare provider offices with custom software found this system cost and effort prohibitive.

Similar systems require a centralized regional repository of medical records. Providers subscribing to the centralized regional repository system send records, as do other provider and hospital systems. Each provider, hospital, and other previous health record source typically have disparate EHR computing systems. The central repository system receives a query from a provider and searches the medical record repository filled with different formatted records to find the requested information. The queried information is reformatted to be compatible with the querying disparate EHR system. Securely sending the health information to the querying EHR system completes the health information exchange, HIE. This system has been clinically trialed and providers found it cumbersome and time-consuming. For the alone and unable to communicate patient with an urgent life-threatening condition, asking health providers to perform a query is inappropriate. Providers always need the previous medical record presented in their SMR formatting. It is appropriate to expect the HIE to provide automated previous medical record information in a usable SMR format for every patient service.

Accordingly, what is needed is an EHR interoperability tool that allows electronic data to be shared between disparate EHR systems to provide a partial pared medical record or an all-inclusive "super medical record" on an emergent basis. The most important time to allow sharing of electronic data occurs during emergencies, when time is of the essence and patients are least likely have the capacity to provide key health information or codes for access to centralized data storage. To be effective, such an interoperability tool and data exchange must allow for emergent and routine easy to exchange electronic health information. The disclosed principles establish simplified universal standard data interchange systems and methods that reduce the cost and effort required to enable EHR data sharing between disparate EHR systems.

SUMMARY

To overcome the deficiencies of the prior art, the disclosed principles can be used in an EHR interoperability tool (herein referred to as "SCUTWORK") that provides interoperability between disparate EHR systems. SCUTWORK uses the standard medical record to label the electronic health record. SCUTWORK creates labeled elemental parts from its source standard medical record and standardizing labeling for each elemental part. Each disparate EHR then uses these standardized labeled elemental parts to divide its entire record into standardized labeled electronic elemental parts with data fields but no data. This creates a universal standard for creating the same labeled elemental parts for every disparate health record. Later, as data is entered into these elemental parts for each disparate EHR, the EHR creates a unique accountability label for each patient service and attaches this to each standard labeled electronic elemental part with data. The result is uniquely labeled standard elemental parts with data strands. As discussed later, the usual structure and operation of the EHR is unchanged by this process. When chosen, structured uniquely labeled standardized elemental parts with data strands can be cut from the disparate EHRs' structure. The resulting unstructured uniquely labeled standardized elemental parts with data strands can be exported to a portable memory device or repository, and subsequently imported into a disparate EHR. The disparate EHR computer system reads the FIC label of each unstructured strand, matches it to its own FIC labeled elemental part, and restructures these strands into the different disparate EHR for that system.

The standard medical record (SMR) has been evolving since the 18$^{th}$ century. SCUTWORK chooses amongst the paper and electronic SMR versions to select the appropriate combination of SMRs from which to create one complete SMR, the source SMR. SCUTWORK creates a method for dividing the entire source SMR into elemental parts.

Once the source SMR is entirely divided into elemental parts, SCUTWORK will label each elemental part with a field indicator code (FIC). There is only one FIC for each elemental part of the source SMR. Each FIC is different from the other FICs of the source SMR elemental parts. The FIC allows for distinguishing between each source SMR elemental part. These FIC labels contain no patient information or data, and are simply a label for the elemental part of the record. The entire source SMR is divided into FIC labeled elemental parts to create one complete set of FIC labeled elemental parts.

SCUTWORK creates a method for concatenating each FIC labeled elemental parts resulting in the entire source SMR divided into concatenated FIC labeled elemental parts.

The disclosed SCUTWORK principles allow interested disparate EHR companies to employ SCUTWORK methods for interoperability of disparate health records of other companies. A SCUTWORK enabled EHR defines a disparate EHR and company that has chosen to employ SCUTWORK methods agreed to follow the SCUTWORK rules for applying SCUTWORK methods, techniques, and processes to its electronic health records.

As defined by SCUTWORK principles, each disparate SCUTWORK enabled EHR company uses the SCUTWORK source SMR concatenated FIC labeled elemental parts as a guide to divide its entire electronic record into corresponding electronic elemental parts. During this process, each of these electronic elemental parts includes a data field, identified by a unique FIC, but no data. Thus, the disparate SCUTWORK enabled EHR company uses the corresponding FICs of the source SMR FIC labeled elemental parts to label each of its electronic elemental parts to divide its entire record into FIC labeled electronic elemental parts.

As defined by SCUTWORK principles, the disparate SCUTWORK enabled EHR company also concatenates each FIC labeled electronic elemental part. During this process, there is no patient information or data contained in any concatenated FIC labeled electronic elemental part. When implementing SCUTWORK principles, the disparate EHR company divides their entire EHR into concatenated FIC labeled electronic elemental parts. Each of the EHR concatenated FIC labeled electronic elemental parts corresponds to only one of the SMR's FIC labeled elemental parts. Once the entire EHR is divided into concatenated FIC labeled electronic elemental parts, the disparate EHR is ready to enter electronic data into these elemental parts.

The SCUTWORK principles, as described herein, is implemented by every SCUTWORK enabled record system in every disparate EHR company. The result is the SCUTWORK concatenated FIC labeled standard elemental parts from the SMR creates a universal standard for each and every disparate EHR, regardless of which EHR company's records system is used. Each disparate EHR company follows SCUTWORK methods and processes, uses the SCUTWORK standard concatenated FIC labeled elemental parts of the SMR to divide each of their entire EHRs into the same standard FIC labeled electronic elemental parts derived from the SMR. Every disparate EHR is now completely divided into standardized concatenated FIC labeled electronic elemental parts. The standardized concatenated FIC labeled electronic elemental parts of any one disparate EHR are the same as those found in any other disparate EHR, regardless of the health record data that is, or will be, entered into this standardized collection of concatenated FIC labeled electronic elemental parts. In this manner, all SCUTWORK enabled disparate EHRs are standardized irrespective of the data in each health record. Even though each and every SCUTWORK enabled disparate EHR is standardized into the same concatenated FIC labeled electronic elemental parts, the usual structure and operation of each disparate EHR will still be different. As electronic data is entered into the EHR, it follows the usual rules of the disparate EHR and the system that initially created that EHR, and is directed to the appropriate electronic fields following the structure and operation of the disparate EHR. The usual structure and operation of the disparate EHR is not changed or altered by SCUTWORK processes. SCUTWORK allows disparate EHR companies to employ SCUTWORK methods and processes, writing them into their software programs for transferring or receiving SCUTWORK based EHRs. The SCUTWORK techniques and resulting processes each EHR company writes into their electronic records software represents additional operations not effecting the usual structure or operation of each disparate company's records software.

Even though each and every SCUTWORK enabled disparate EHR is standardized into the same concatenated FIC labeled electronic elemental parts, the usual structure and operation of each disparate EHR will still be different. As electronic data is entered into the EHR, it follows the usual rules of the disparate EHR and the system that initially created that EHR, and is directed to the appropriate electronic fields following the structure and operation of the disparate EHR. The usual structure and operation of the disparate EHR is not changed or altered by SCUTWORK processes. SCUTWORK allows disparate EHR companies to employ SCUTWORK methods and processes, writing them into their software programs for transferring or receiving SCUTWORK based EHRs. The SCUTWORK techniques and resulting processes each EHR company writes into their electronic records software represents additional operations not effecting the usual structure or operation of each disparate company's records software.

The first data entered for any patient service is registration information. The registration data represents accountability information. The registration data fields for any one service are used to create accountability information identifier (A-I) labels. SCUTWORK provides a technique for allowing accountability information from each patient service to create a unique A-I label. Each A-I label includes but is not limited to information about patient, provider, location of service, time of service, date of service, and, when indicated, standard medical/billing/procedure code or pre-existing code information for the patient service. Thus, the accountability information produces a unique A-I label for each patient service.

SCUTWORK allows each disparate EHR company to employ the above SCUTWORK principles for creating A-I labels based on the accountability information associated with a patient service. Each disparate EHR company writes code into its software to allow for the A-I. As data regarding a patient service is entered into a disparate electronic health record, the accountability information data fields are collected to produce an A-I for that patient service. As data is entered into each concatenated FIC labeled elemental part, the A-I label is added to each concatenated FIC labeled elemental part. The result is a concatenated strand of A-I+FIC standard elemental part with data. The result of data entering into the disparate EHR during any one patient service is the creation of one or more concatenated strands of A-I+FIC standard elemental parts with data, each part having data pertaining to that patient service.

The A-I consists of accountability information which uniquely identifies each patient service, and the FIC is the standardizing label for every elemental part. As such, a FIC labels each elemental part of a SCUTWORK EHR, while an A-I labels the data entered into each elemental part. Adding the unique A-I label to the standard FIC label creates a uniquely labeled standardized elemental data strand different from all other uniquely labeled standardized elemental data strands. Each SCUTWORK enabled disparate EHR is comprised entirely of unique strands comprising concatenated A-I+FIC standard elemental parts with data.

Adding the A-I to the FIC creates a permanently bonded A-I+FIC as well as a permanently bonded concatenated A-I+FIC standard elemental part+data strand. Once this uniquely labeled standardized elemental data strand is created, it remains a permanently bonded single unit and subsequent modification is not allowed.

When data is entered into an EHR during any one patient service, there may be portions of the EHR requiring more than one specific FIC labeled electronic elemental part. For instance, in one patient service, there may be more than one diagnosis. Allow Dx to represent the FIC of the diagnosis elemental part of the source SMR. There is only one Dx-FIC labeled electronic elemental part. When a diagnosis is added to an EHR, an ICD-10 code (International Classification of Diseases, Tenth Revision) is used in the A-I label. This ICD-10 code will be utilized in the A-I as standard pre-existing code information. When data is entered as more than one diagnosis, more than one Dx-FIC standard electronic elemental part will be generated. Each diagnosis added has the same Dx-FIC label, since the each of these elemental parts of the record are for "diagnosis", but they are distinguished from each other using the A-I containing the ICD 10 code. Using the disclosed SCUTWORK process during one patient service, data entered into the patient's medical record as multiple diagnoses can be used to create multiple uniquely labeled standardized elemental data strands (recalling that such a strand is comprised of FIC label+A-I label+data) which have the same Dx-FIC label but different A-I labels. For instance, diagnoses of a viral syndrome with ICD-10 code B34.9 and essential hypertension with ICD-10 code I10 for a single patient encounter would result in two diagnosis uniquely labeled elemental data strands, one A-I label including B34.9 and a second A-I label including I10 (while each strand would have the same FIC label for the elemental part of the EHR called "diagnosis"). This would be the case even if other portions of the A-I labels are the same, such as patient name, provider name, and location, date and time of service.

The process of using SCUTWORK universal standard division of each disparate EHR into concatenated FIC-labeled elemental parts and the creation and attachment of the A-I and data to the concatenated FIC-labeled elemental parts does not change the usual structure or usual operations of the disparate EHR. SCUTWORK provides guidelines for FIC-labeled elemental parts and A-I and data attachment in the disparate EHRs. The disparate EHR companies are responsible for writing code into their software programs to follow these SCUTWORK guidelines.

When the provider chooses which portion of the disparate EHR to share, that portion of the EHR is copied and cut into unstructured unique concatenated strands of A-I+FIC standard elemental parts with data. These unstructured strands of unique concatenated A-I+FIC standard elemental parts with data can be easily exported and later imported into other disparate EHR systems if the receiving system includes the SCUTWORK protocol. The provider and patient choose which HIPAA (Health Insurance Portability and Accountability Act) approved method or methods of sharing to use. For instance, SCUTWORK unstructured uniquely labeled elemental data strands exported and stored on portable storage devices can be carried by the patient to enable sharing of medical records between non-connected and dissimilar disparate EHR systems. In some embodiments, smart card features on a portable memory device can allow for connectivity and ease of access to central or cloud record repositories for large data items such MRIs, CATs, angiograms, etc.

The unstructured uniquely labeled standardized elemental data strands contain all the information necessary for any disparate SCUTWORK enabled disparate electronic health record system to reassemble the unstructured strands into a different disparate EHR. As a matter of record, a single unstructured uniquely labeled standardized elemental data strand contains all the information needed to be placed into any SCUTWORK enabled disparate electronic health record. The standard FIC label informs the disparate health record system where to place the data strand in its FIC standardized structure. The A-I provides permanent unique accountability information for each patient service. The A-I is unique for each patient service as it provides unique information like the name of the author (provider), date (and perhaps time) of service, date of birth of the patient, location of service, and could also include a standard or pre-existing medical code. When indicated, pre-existing code information is added to the A-I, providing unique information different from all other A-I labels. Combining the FIC and A-I produces a permanent bond and labeled standardized elemental data strand as one unit. The receiving disparate electronic health record system reads and recognizes the unstructured concatenated A-I+FIC standard electronic elemental part with data strands and places them into its structure utilizing its matching standardized FIC labels.

SCUTWORK provides guidelines for cutting structured concatenated A-I+FIC standard electronic elemental part with data strands into unstructured concatenated A-I+FIC standard electronic elemental part with data strands. It also provides guidelines for exporting, transmitting, importing, and reassembling the unstructured concatenated A-I+FIC standard electronic elemental part with data strands back into a structured EHR. The disparate EHR companies are responsible for writing code into their software programs to follow these SCUTWORK guidelines.

By creating strands of unstructured concatenated A-I+FIC standard electronic elemental part with data in the disclosed manner, transferred data is unstructured and does not contain a specific format or other structure, since that would limit the ability of another health record system to read/interpret the data. Instead, existing EHR systems can be updated to both export and import medical records using SCUTWORK processes by simply a software update. Such an update would allow the updated EHR system to read and interpret the unstructured data strand's A-I+FIC and then properly rebuild the EHR, which then includes the data in each rebuilt FIC labeled elemental part. Once an EHR system is enabled with SCUTWORK processes, there is no need to create conversion or exchange software to enable importing or exporting EHR records between two paired but incompatible EHR systems.

When another disparate EHR system receives the unstructured concatenated uniquely labeled standardized electronic data strands disclosed herein, the disparate EHR system reads each unstructured concatenated uniquely labeled standardized electronic data strand, recognizes the A-I+FIC showing it is permanently bound, recognizes the FIC and enters it into its matching structured FIC labeled disparate electronic elemental part. After reading the unstructured data strand, the receiving disparate EHR system follows instructions from its provider as to which and how unstructured concatenated uniquely labeled standardized electronic data strands will be filed.

SCUTWORK provides a simple and inexpensive method for allowing interoperability among disparate medical record systems. Using the standard medical record to label the electronic files allows for the most beneficial SCUTWORK functions, including but not necessarily limited to, a "super medical record" that starts at birth and ends at death; immediate interoperability of the medical record for life-threatening emergencies; and the ability of providers to select specific types of records such as immunizations or a patient's white blood cell count over time. The ability to verify the existence and accountability of specific types of records helps avoid unnecessary duplication of services and will reduce if not eliminate the more than 25 billion dollars of medical waste a year by having access to the entire medical record when it is needed by the medical service provider.

Disparate EHR companies write code into their software to employ the disclosed SCUTWORK principles. SCUTWORK principles enable disparate EHR systems to transform their records from 100% structured data to 100% unstructured data and back again into 100% structured data. It does so without changing the basic structure or operation of any involved EHR. It does so without a third software program, a third party, third computer system, or Health Information Exchange, HIE. Moreover, as a first healthcare provider creates or updates an EHR of a patient, that data is structured data within that healthcare provider's EHR system. When the EHR information is stored on behalf of the patient, the disclosed principles via the SCUTWORK principles allow storing the patient's medical records as unstructured data. When any part or all of that medical record of the patient is accessed by a second healthcare provider, his/her SCUTWORK enable EHR system converts the stored unstructured data back into structured data that is compatible with the system/format of the second healthcare provider.

This simplifies electronic interoperability to only disparate EHRs with structured FIC standard labeling and strands of uniquely concatenated A-I+FIC standard electronic elemental parts with data and unstructured concatenated A-I+FIC standard electronic elemental parts with data strands. SCUTWORK enabled disparate EHRs eliminate all third-party software programs, third-party computers and Health Information Exchanges, HIEs. Although SCUTWORK provides techniques, processes, and quality monitoring, SCUTWORK does not write disparate health record software, nor does it provide a third software or computer system to allow for interoperability. These distinguishing features of SCUTWORK are not limited to only the health field; any professional field that uses uniformly standardized records can benefit from the principles provided by SCUTWORK.

Numerous embodiments and advantages associated with each such embodiment are discussed in further detail below.

BRIEF DESCRIPTION OF THE DRAWINGS

The detailed description that follows, by way of non-limiting examples of embodiments, makes reference to the noted drawings in which reference numerals represent the same parts throughout the several views of the drawings, and in which:

FIG. 1 illustrates a listing of an exemplary source standard medical record's personal registration FIC labeled elemental parts that may be used to standardize EHRs within the SCUTWORK framework.

FIG. 2 illustrates disparate EHR-1's and EHR-2's structured concatenated FIC labeled electronic elemental parts of personal registration with data fields, but no data, representing exemplary standardized personal registration information, in accordance with SCUTWORK principles disclosed herein.

FIG. 3 illustrates personal registration information of EHR-1 of FIG. 2 after data has been entered in each FIC labeled elemental part, resulting in the generation of the A-I label of a patient visit and its addition to the FIC labeled elemental parts to create structured concatenated A-I+FIC standard electronic elemental parts with data strands.

FIG. 4 illustrates how the structured concatenated A-I+FIC standard electronic elemental parts with data strands are extracted from EHR-1 of FIGS. 2 and 3 to create unstructured concatenated A-I+FIC standard electronic elemental parts with data, and are transferred to a portable storage device.

FIG. 5 illustrates how the unstructured concatenated strands of A-I+FIC standard electronic elemental parts with data on the portable storage device are transferred to disparate EHR-2's system, read by EHR-2's system, matched to EHR-2's FIC standard labels, and inserted into EHR-2's structure to created structured concatenated A-I+FIC standard electronic elemental parts with data.

The above-referenced figures are provided herein for the purpose of illustration and description only and are not intended to define the limits of the disclosed principles.

DETAILED DESCRIPTION

In view of the foregoing, through one or more various aspects, embodiments and/or specific features, the present disclosure is intended to bring out one or more of the advantages that will be evident from the description. The present disclosure makes reference to one or more specific embodiments by way of illustration and example. It is understood, therefore, that the terminology, examples, drawings and embodiments are illustrative and are not intended to limit the scope of the disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

The disclosed principles provide systems and methods that rely on labeling an electronic record with a standard medical record. This requires the source standard medical record (SMR) to be divided into elemental parts that become the standard for the division of all disparate electronic health records (EHRs) into elemental parts. The elemental parts of the SMR are labeled with a distinct field indicator code (FIC) for each part, and these become the universal standard for FIC labeling of all disparate EHR electronic elemental parts. The disparate EHR's standardized FIC labeled elemental parts are concatenated in the same manner, creating standardized concatenated FIC labeled electronic elemental parts for all disparate EHRs. The extraction of accountability individual fields from an EHR creates an accountability information identifier (A-I) uniquely labelling all data for any one patient service. As data is entered, the A-I is created and data+A-I are added to an appropriate FIC standard electronic elemental part. The combination of the A-I and FIC uniquely labels each and every concatenated electronic elemental part and the data therein. The portion of the EHR to be shared is selected by the provider, cut into unstructured uniquely labeled concatenated A-I+FIC standard electronic elemental parts with data, and stored as a separate file external to the EHR system. Using HIPAA compliant methods, the unstructured elemental data strands (each comprised of A-I+FIC+data) are transferred to a second different disparate EHR system enabled with SCUTWORK principles. The disparate EHR system reads the unstructured data, recognizes the standardized FIC labels, and matches and places each unstructured concatenated A-I+FIC standard electronic elemental parts with data into its standardized FIC structure.

The source SMR is derived from the best found examples of the standard medical records. SCUTWORK chooses which combination of electronic and paper source medical records to use. SCUTWORK combines these choices to create a complete standard medical record, or the source standard medical record. This source standard medical record becomes the standard structure for all EHRs deconstructed or reconstructed using the SCUTWORK principles.

To do this, the SCUTWORK principles divide the source standard medical into elemental parts. The source standard medical record is completely divided into elemental parts. Every elemental part is different from the other elemental parts.

The SCUTWORK principles create an FIC for each elemental part of the source standard medical record. FIG. 1 illustrates FIC labeled elemental parts of the personal registration information, 100, of the source standard medical record that may be used as part of the universal standard of the SCUTWORK framework. In FIG. 1, 101 illustrates the FIC for elemental part "Last Name". The source SMR's FIC labeled elemental parts have no data fields and no data. The first data entered for any patient service is registration information. The registration information data represents accountability information. The accountability information in the registration data fields for any one service are used to create the A-I.

Each disparate EHR company uses the FIC labeled elemental parts derived from the source SMR as the universal standard from which to divide its electronic record into elemental parts, in accordance with the SCUTWORK principles. As such, each disparate EHR company uses the corresponding FIC of each of the source SMR's elemental parts to label each of its corresponding elemental parts. These FIC labeled electronic elemental parts have data fields but no data yet. As each EHR company has used the FIC labeled source SMR elemental parts to divide its record into FIC labeled electronic elemental parts, every EHR is divided into the same standardized FIC labeled electronic elemental parts. The choice to employ the disclosed SCUTWORK principles resides with each EHR company. Each EHR company must agree to follow SCUTWORK rules and agree with SCUTWORK terms to be allowed to write these methods and techniques into their software programs. The EHR company that agrees to these rules and terms is SCUTWORK enabled.

FIG. 2 illustrates two disparate electronic health records, EHR-1 300 and EHR-2 500, which have their registration information divided into concatenated FIC labeled elemental parts in accordance with the disclosed principles. In FIG. 2, 102 shows the structured concatenated Date of Birth FIC standard elemental parts of EHR-1 and EHR-2. 103 represents structure of the EHRs. Each EHR is composed of structured concatenated FIC standard elemental parts, but some EHRs will have different FIC labeled elemental part composition. Although every EHR will be composed of the same standardized FIC labeled elemental parts, the structure, shown by 103, and operations of each EHR within their respective originating computer systems will not be altered by the addition of FIC labels or the division into elemental parts as disclosed herein.

The registration information is entered before any other data for a specific patient service. The registration elemental parts provide accountability information needed to create the A-I for any one patient service. In exemplary embodiments, the minimal information needed to create the A-I is the patient personal information (e.g., name and DOB, etc.), provider information (e.g., provider name, facility name, location of service, etc.), and when the medical service was performed (e.g., date, time, etc.). This information comes from registration, and these data fields will be available with the first entry of data for any patient service. The combination of patient information, provider information, and date creates a unique A-I label for any one patient service. As data is entered for any one patient/health service, the A-I is generated and can be used to label each data entry for that patient service. All data entered during one patient service is labeled with the unique A-I identifying that patient service.

As data is entered into a concatenated FIC labeled elemental part, the unique A-I for that service is added to the data in each FIC. FIG. 3 illustrates personal registration information of EHR-1 after data has been entered in each concatenated FIC labeled elemental part, resulting in the generation of the A-I label of a patient visit and its addition to the FIC labeled elemental parts to create structured concatenated A-I+FIC standard electronic elemental parts with data, see 104. FIG. 3 shows that when the registration/accountability data is entered into EHR-1, the A-I is generated and added to each of the FIC labeled electronic elemental parts at the same time the data is entered into the elemental part. The A-I label that has been generated and added to FIC label 102 (which in this example is "First Name"), and 105 is the data in that FIC, "John." Adding the A-I+data to the concatenated FIC labeled elemental parts produces data strands of concatenated A-I+FIC electronic elemental parts with data, an example being 104.

Key fields are extracted from the EHR from each of the types of information, and combined to create an accountability information identifier/code used as a label to tie extracted data fields to a specific EHR. The A-I label can be used as a fixed length header at the start of each extracted data set to allow identification of all data sets/files related to a specific EHR. Each A-I field may be a fixed length, so the resulting A-I code/label would also be of a fixed length which would make it easier to parse. A careful design of the field labeling may be done to include all potential data type fields so that no data is lost when being exchanged between disparate EHR systems. Each field could be separated by a unique character, such as an exclamation point, which would not appear within normal data (e.g., not a period), followed by a termination character to indicate the end of the A-I string, such as a tilde (~), as illustrated in FIG. 3.

Special circumstances occur when there is more than one type of FIC labeled electronic elemental part needed for a patient encounter/service. For example, in embodiments where there is data and time, an encounter that requires more than one blood pressure measurement would be uniquely identified and distinguished by the time. There are instances where more than one type of FIC labeled elemental part will be needed and generated. Most commonly, this will occur with multiple diagnoses and medications. To allow each A-I+FIC label to remain unique for diagnoses, the ICD 10 code for the specific diagnosis may be added to the A-I label. For medications, the National Drug Code may be used. The A-I label is a specific length, so a 15-digit A-I sequence is added for diagnosis and medications. When all or part of this is not needed, the additional characters may simply be filled with 0s.

Excluding the special circumstances of the prior example, there is only one type of FIC label for each patient service. When more than one type of FIC label is needed for each patient service, the 15-digit A-I sequence may use pre-existing standard labeling to distinguish between the different type of FIC labels. In such embodiments, the A-I uniquely labels all data entry for a single patient service. When the A-I is bonded to the FIC, the A-I+FIC is unique as there is only one FIC for every patient visit and the A-I uniquely identifies each patient service. As above and for medical record parts using more than one type of FIC per service, the A-I also uniquely labels and distinguishes between different diagnoses and medications. The bonded A-I+FIC provides a unique label for every electronic elemental part for every service that is different from all other labels used by the same EHR, as well as all other disparate EHRs.

Rules within the SCUTWORK principles disclosed herein state that the A-I+FIC union is bonded and the concatenated A-I+FIC labeled electronic elemental parts with data strands are permanent. Thus, SCUTWORK rules prohibit modification of any concatenated A-I+FIC labeled elemental parts with data strands, and thus each of these results in a SCUTWORK defined unalterable data strand.

The provider chooses which portions of the EHR to copy, share with the patient, or export to another entity. The provider may choose which portions of the record to copy before, during, or after the patient service. FIG. 4 illustrates the exporting of unstructured concatenated A-I+FIC labeled electronic elemental parts with data to a portable storage device, in accordance with the disclosed principles. As illustrated in FIG. 4, portions of the record EHR-1 discussed above are selected, copied, and the structure cut to form unstructured data strands comprising concatenated A-I+FIC labeled electronic elemental parts with data therein. 106 shows the selected portion of the record and 107 shows the copied and cut unstructured elemental part strands. This file of unstructured concatenated A-I+FIC labeled electronic elemental parts with data strands can be transferred, shown by 108, to a portable storage device 109, or even just temporary file, and/or exported to distant storage electronic system using HIPAA approved methods. Using HIPAA approved methods, the data files can be stored on any type of storage device, including portable devices 109, that can be used to share data between non-connected EHR systems, as well as other forms of local, centralized, distributed, or cloud-based storage and access systems. Storing the data on portable memory devices allows ready access to a patient's medical records, and can be carried or worn by a patient with a known medical condition, so as to allow medical history information to be readily available even in emergency and life-critical situations. Adding smart card features to the portable memory device allows easier access to centralized and cloud-based storage of data sets too large to be included on the portable memory device, such as MRIs, CATs, angiograms, etc. By adding smart card features to the portable memory device, centralized storage and cloud-based operation allows access to medical records by all affiliated providers, and system enhancements and bug fixes can be made available remotely and at the same time to all organizations that use the system.

FIG. 5 illustrates importing, shown by 110, unstructured concatenated A-I+FIC labeled electronic elemental parts with data strands stored in the portable storage device 109 into EHR 2 500 of FIG. 2. The electronic records system associated with EHR-2 reads the imported data strands and matches the FIC labels to its own FIC standard labels in accordance with the SCUTWORK principles discussed above. The matched FIC standard labels allow the unstructured strands of elemental parts with data to be inserted into EHR-2's structure. Importantly, the structure of EHR-2 need not be the same as that of EHR-1, as illustrated by the "provider" name in EHR-2 being at the beginning of the health record, while the "provider" name stored in EHR-1 was in a different structure location within the health record. The provider of EHR-2 chooses how to manage the imported unstructured data strands. The unstructured data chosen is placed into EHR-2's structure using matching FIC labeled electronic elemental parts. In the illustrated example of FIG. 5, the receiving records system of EHR-2 is importing/employing all of the data strands from EHR-1 of FIG. 4 on the portable memory device to create new patient registration information; however, in other embodiments only some of the data from EHR-1 may be used.

Therefore, as disclosed herein and in accordance with the SCUTWORK principles, an EHR can be reconstructed from a set of data files stored as unstructured uniquely labeled data strands. The A-I code is used to identify all files associated with a specific original EHR/medical service or patient encounter. The FIC identifies the universal standardized elemental EHR part source field for the data in the file. This configuration allows for reconstruction of an EHR from a set of unstructured data files regardless of the structure and order of fields (i.e., formatting) used in a particular EHR computer system. The combination of the A-I code with the FIC allows a differently structured EHR computer system to correctly reconstruct a patient's EHR from the individual data files/strands created and saved in accordance with the disclosed principles.

Accordingly, SCUTWORK techniques can be used by disparate EHR computing systems to create A-I labels and the FIC universal standard electronic elemental parts, all following a single, standardized set of rules under the SCUTWORK framework. The uniquely concatenated data strands of A-I+FIC standard elemental parts with data can be cut from their EHR structured string data tree and stored randomly (unconnected and unstructured) on a patient-secured storage medium. The SCUTWORK tool is used to cut the structured string data trees of conventional EHRs to produce randomly saved unstructured A-I-labeled data sets on the storage device, and to reorganize randomly saved A-I labeled data sets from the patient's storage device into its string data tree to reconstruct the EHR. A different, subsequent SCUTWORK-capable EHR system can then identify the storage medium's FIC standard elemental parts with data strands and place them into its string data tree. The disclosed principles permanently label every elemental data strand of the EHR using A-I accountability information combined with FIC, which then allows the SCUTWORK-labeled data strands/sets to be shared with any other SCUTWORK enabled EHR system. Stated another way, a SCUTWORK enabled system can identify the A-I+FIC of each data strand and reassemble the data in those strands into the different shaped data tree of a different EHR system.

Additionally, existing EHR systems can be updated to both export and import medical records using the SCUTWORK format and techniques by simply a software update. Once an EHR system is updated with SCUTWORK capabilities, there is no need to create conversion or exchange software to enable importing or exporting EHR records between two paired but incompatible EHR systems. One may initially think that updating a records system with SCUTWORK capabilities is the same thing as using conversion or exchange software, but it is not. Conversion software requires the capability to convert multiple EHR formats into the local system's format, whereas SCUTWORK does not. Also, conversion software works by reading a different EHR format and changing that disparate format into the unique format of the converting system, whereas SCUTWORK does not. Instead, SCUTWORK extracts data from any EHR format and provides it in a single, unstructured set of data strands, where those strands may be read by a SCUTWORK-enabled system and reassembled to any desired format. In short, conversion and exchange software take data in one format and converts it to another format, whereas SCUTWORK removes any data format by converting the information in an EHR into unstructured data strands that can later be placed into a particular format, when needed. In addition, SCUTWORK facilitates less expensive EHR systems so they can be utilized by small practices. Only systems that are not SCUTWORK enabled need to be modified. Existing systems can be updated. Relatively quick software development is all that is needed to add SCUTWORK functionality to existing EHR systems due to the simplicity of the concept.

Furthermore, the disclosed principles allow for the traditional technique of saving health records separately based on location; however, the disclosed principles provide for labeling all information produced with the identifying information regarding the professionals authoring the data. The provider, with patient permission, may select none, part, or all of the record to share using SCUTWORK principles. For example, SCUTWORK may label every part of the medical record with location, date, time, and the name of its author. Unique labeling of elemental data sets with such accountability information means the author responsible for the entry will be permanently recorded. All subsequent users of the information will have access to this information since it is permanently encoded in the A+I label of the data strands. This gives recognition of the entry of information to the author, who by allowing the information to be included in the SCUTWORK portable data storage device, gives permission for the patient to share this with other health providers, health plans, and health clearinghouses. This will improve the transparency and responsibility of the electronic health record.

Consequently, this can allow all records to be combined into one "super record" of medical events of a patient, regardless of the provider, event location, or procedure type. Patient data can be stored in the SCUTWORK format over a period of time, including a person's entire lifetime, to allow for storing a complete historical medical record. In this way, a provider allowed access by the patient can immediately see all services the patient has received his/her entire life, as well as when, by whom and where the service was performed. This allows all of the record to be discovered and for most, if not all, of the resources wasted by duplication of services to be eliminated.

Since each elemental medical procedure (such as, but not limited to, inoculations or blood pressure) are stored separately and labeled to identify the specific procedure, it is possible to scan through historical records to select these specific procedures in order to compile a comprehensive historical record. Thus, SCUTWORK enabled systems can select and import only the information needed from a group of SCUTWORK coded files, such as specific vaccination records. What information is included on the portable storage device will be the choice of the health care provider and patient. With SCUTWORK, the information from each of these electronic records could be kept separate or, as the provider chooses, they could be combined to make a super record.

For example, if the user wanted to see the patient's chronologic presentation of white blood cells, they could see a lifelong complete listing. A patient's entire life's vaccination history from all locations could be seen on one page using the deconstruction and reconstruction of data sets from EHRs provided by the disclosed principles. For example, searching for multiple occurrences of the same procedure, such as a pneumonia vaccine immunization over a period of years, would be relatively fast by searching an individual's SCUTWORK-created records for a particular procedure, such as a specific A-I having a Healthcare Common Procedure Coding System (HCPCS) HCPS code. The HCPS codes are a set of health care procedure codes based on the American Medical Association's Current Procedural Terminology (CPT). Individual medical services, procedures, equipment, etc. may be categorized and labeled by such a standard medical code within the SCUTWORK format. Using a standard medical coding system to identify specific types of SCUTWORK data files provides a fast and easy way to identify specific types of SCUTWORK health records.

Additionally, SCUTWORK-created unstructured data files may function with local, portable, or cloud storage of the SCUTWORK patient data records. SCUTWORK EHR data can be exported and stored on portable storage devices which can be carried by the patient. For the case of portable storage carried by the patient, SCUTWORK facilitates emergency access to the patient's data record at all times, since the patient can carry their own medical history with them, and there is no need to have access to an external database system to gain access to their medical records. For example, SCUTWORK-based patient portable storage devices can be created holding their medical records. The patient secured portable storage device allows the patient to choose what level of security they want for their health records. For example, for those who choose the same security as for their driver's license, credit cards, and social security number, then it could be kept without a password or code in their wallet for immediate access of the health record by health care workers in emergency circumstances. However, for those patients wishing high security then it could have a password and/or code limiting access to only those they consciously choose to share this information. For emergency situations, the patient-created security could be biometric, such as a fingerprint scan or a facial recognition scan, where the patient's portable records can still be accessed if the patient is unconscious or similarly incapacitated. The emergency personnel can use the device to immediately access the medical record and discover allergies, medications, and medical problems that could be potentially lifesaving.

Labeling data records in accordance with the SCUTWORK principles is not necessarily limited to the field of healthcare or patient health records. The disclosed SCUTWORK systems and methods are an electronic record Rosetta Stone for any standardized record keeping profession. This includes the fields of health care, finance, law enforcement, engineering, accounting, banking, and so on. The SCUTWORK labelling of exported data sets/files can be applied to other fields, such as but not limited to, engineering, architecture, banking, teaching, and construction. As such, SCUTWORK is designed for all standard record professions. Thus, SCUTWORK labeling can be applied to various fields that use similar standardized reporting where data interchange between incompatible systems is needed. Conventionally, when such standard record is made into an electronic record, all differently structured data electronic record versions will have similar record organization and formatting, but not similar structured electronic data organization. SCUTWORK uses a standard record to develop universal standard elemental parts, and labels each of those standard elemental parts. A SCUTWORK enabled disparate electronic record system uses FICs to uniquely label electronic elemental parts with data fields but no data. The standard FIC labeled elemental part of any electronic record is necessary for the application of an A-I label to be unique. The structured data of each different electronic record can be reduced to unstructured data (without being a complete patient record) in accordance with the disclosed principles. This labeled unstructured data can then be reorganized back into a different electronic record having the exact same information as the EHR from which the unstructured data was derived.

Based on the above, exemplary aspects in accordance with the disclosed principles may comprise one or more of the following principles:

An interoperable healthcare data exchange method for enabling transferring of Electronic Health Records (EHRs) between incompatible EHR computer systems, the method comprising:
  identifying a source standard medical record (SMR);
  identifying elemental parts of the source SMR;
  creating a Field Indicator Code (FIC) to identify each elemental part of the source SMR;
  using the FIC labeled elemental parts of the source SMR to create electronic elemental parts within a source EHR;
  identifying each electronic elemental part of the source EHR using the FIC of the corresponding SMR's elemental part;
  concatenating each FIC electronic elemental part of the source EHR.

Additional principles include dividing disparate EHRs into FIC electronic elemental parts using the FIC elemental parts of the SMR thereby creating universal standardization of EHRs:
  as data is entered for any one patient service, multiple key EHR fields create an Accountability Information Identifier (A-I) label that uniquely identifies the same patient service;
  as data is entered into a FIC elemental part, the created A-I is bonded to the FIC elemental part to create unique, structured bonded concatenated A-I+FIC electronic elemental part/s with data;

each structured concatenated data strand or string is thus an individual data file, wherein each said data file can be reassemble in the importing disparate EHR by matching the FIC standard labels of the unstructured concatenated data strings to the FIC electronic elemental parts of the importing EHR.

In some embodiments, each unique A-I code is a fixed length.

In some embodiments, each such FIC is a text string.

In some embodiments, each such FIC is a number.

In some embodiments, each concatenated strand or string is saved on a portable device.

A method of reconstructing an EHR from individual files previously exported from an EHR system, the method comprising:

identifying unstructured data strands having a unique A-I+FIC header;

reading each identified data strand and identifying the type of data stored within each data strand by using an FIC included in each data strand; and reading the data within each identified data strand using the A-I label in each A-I+FIC header storing the read data in a corresponding data field of an EHR, each corresponding data field being identified by the FIC label contained within the data strand header.

In some embodiments, a new EHR is created and populated with the information contained within each data strand/file.

In some embodiments, an existing EHR is updated with the information contained within each data strand/file.

The FIC standard label for each and every disparate electronic health record elemental part combined with the unique A-I label for any one patient service creates a unique A-I+FIC standard label different from all other A-I+FIC standardized labels in the same or any other disparate health records, acknowledging that when more than one FIC labeled electronic elemental part is required, for example when more than one diagnosis is made, then standard code or pre-existing code information is added to the A-I of each structured concatenated A-I+FIC standard electronic elemental part with data strand allowing the A-I+FIC standardized label to remain unique.

Throughout the SCUTWORK principles disclosed, each disparate health record maintains its usual electronic structure and operations different from all other disparate health records.

Before, during, or after the patient service, the provider chooses which, if any, parts of the disparate electronic health record to export.

The structured electronic health record information selected for export, composed of structured concatenated uniquely labeled A-I+FIC standard electronic elemental parts with data strands, are saved and then cut by the disparate electronic health record into unstructured bonded concatenated uniquely labeled A-I+FIC standard electronic elemental part with data strands.

The A-I+FIC label is unique making the unstructured concatenated uniquely labeled A-I+FIC standard electronic elemental part with data strand unique and different from all other unstructured uniquely labeled standard electronic data strands, both in the same EHR or any other disparate EHR.

The patient and provider choose which acceptable HIPAA method will be used to export electronic health record information.

The unstructured bonded concatenated unique A-I+FIC standard electronic elemental parts with data strands are exported using the acceptable HIPPA method.

After the importing, the EHR reads each imported unstructured data strands and it:

follows instructions from its provider as to which and how unstructured concatenated uniquely labeled standard electronic data strands will be filed;

recognizes each unstructured bonded A-I+FIC standard label and reassembles each unstructured data strand into its matching structured FIC labeled standardized electronic elemental part to create structured bonded concatenated A-I+FIC standard electronic elemental electronic parts with data.

The methods and processes of the SCUTWORK principles simplifies EHR interoperability to universally standardized FIC labeled disparate electronic health records, creating and applying a unique A-I label for each patient service, and unstructured bonded concatenated unique A-I+FIC standard electronic elemental parts with data strands.

To verify uniform application, additional methods and processes are created to monitor the implementation of methods and processes disclosed herein.

The foregoing description has made reference to several exemplary embodiments. It is understood, however, that the words that have been used are for description and illustration, rather than words of limitation. Thus, the present embodiments are therefore to be considered in all respects as illustrative and not restrictive. Changes may be made within the purview of the appended claims, as presently stated and as amended, without departing from the scope and spirit of the disclosure in all its aspects. All changes which come within the meaning and range of equivalency of the claims are therefore intended to be embraced therein. Although this description makes reference to particular means, materials and embodiments, the disclosure is not intended to be limited to the particulars disclosed; rather, the disclosure extends to all functionally equivalent technologies, structures, methods and uses such as are within the scope of the appended claims. Further, the recitation of any method steps does not denote a particular sequence for execution of the steps. Such method steps may therefore be performed in a sequence other than recited unless the particular claim expressly states otherwise.

In the numerous embodiments of the inventive subject matter disclosed herein, such embodiments may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Moreover, the Abstract is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus, the following claims are hereby incorporated into the Detailed Description, with each claim standing on its own as a separate embodiment.

The invention claimed is:

1. A computer-based method for standardizing disparate Electronic Health Records (EHRs) so that the EHRs are communicable and presentable on computing devices across a network that have inconsistent formatting of EHRs, the method comprising:
   identifying, using a computing device comprising one or more processors, a Standard Medical Record (SMR), wherein the SMR comprises elemental parts, each elemental part representing a unique data field of the SMR;
   creating, using the computing device, a distinct unique Field Indicator Code (FIC) for each elemental part of the SMR;
   identifying, with the computing device, each corresponding elemental part of a source EHR using each corresponding FIC of the SMR's elemental parts;
   deconstructing, with the computing device, the source EHR into its identified elemental parts;
   creating, with the computing device, an Accountability Information Identifier (A-I) for all data stored in the elemental parts of the source EHR pertaining to any one patient service, each A-I derived from accountability information represented by said data pertaining to said one patient service in corresponding elemental parts, and including at least patient information, health provider information, and health service information;
   creating, with the computing device, an unalterable data strand for each elemental part, and corresponding data stored therein, of the source EHR, each said created data strand labeled, by the computing device, with a corresponding FIC and A-I; and
   concatenating, with the computing device, each A-I+FIC-labeled data strand of the source EHR.

2. The method of claim 1, wherein the data fields corresponding to each of the elemental parts are selected from the group consisting of: patient name, patient address, patient social security number, patient date of birth, date of a health procedure or event, type of health procedure or event, medical code of a health procedure or event, date of a health procedure or event, time of health procedure or event, report associated with a health procedure or event, provider name, provider identification number, or provider location.

3. The method of claim 2, wherein the data in the data fields corresponding to each of the elemental parts represents information selected from the group consisting of: patient name, patient address, patient social security number, patient date of birth, date of a health procedure or event, type of health procedure or event, medical code of a health procedure or event, date of a health procedure or event, time of health procedure or event, report associated with a health procedure or event, provider name, provider identification number, or provider location.

4. The method of claim 1, wherein accountability information regarding patient information comprises patient's first name, patient's last name, patient's street address, patient's city of residence, patient's state of residence, patient's social security number, patient's telephone number, patient's date of birth, and patient's insurance coverage.

5. The method of claim 1, wherein accountability information regarding provider information comprises provider's first name, provider's last name, provider's street address, provider's city, provider's state, provider's license number, and provider's telephone number.

6. The method of claim 1, wherein accountability information regarding health service information comprises health service type, health service medical procedure code, health service billing code, location where health service was provided, date of health service, time of health service, results of health service, and report associated with health service.

7. The method of claim 1, wherein the A-I for the data stored in one elemental part of the source EHR and the A-I for data stored in another elemental part of the source EHR are the same A-I.

8. The method of claim 1, wherein each FIC comprises at least part of a header for each corresponding data strand.

9. The method of claim 1, wherein each A-I comprises at least part of a header for each corresponding data strand.

10. The method of claim 1, wherein all A-Is for each data strand comprises a single fixed length.

11. The method of claim 1, wherein each FIC for each data strand comprises a text string.

12. The method of claim 1, wherein each FIC for each data strand comprises a fixed-length number.

13. The method of claim 1, further comprising, for a plurality of disparate EHRs:
   identifying, with the computing device, each corresponding elemental part of each of the plurality of disparate EHRs using each corresponding FIC of the SMR's elemental parts;
   creating, with the computing device, an Accountability Information Identifier (A-I) for all data stored in the elemental parts of each of the plurality of disparate EHRs pertaining to any one distinct patient service for each disparate EHR, each A-I derived from accountability information represented by said data pertaining to said one patient service in corresponding elemental parts of each of the plurality of disparate EHRs, and including at least patient information, health provider information, and health service information;
   creating, with the computing device, an unalterable data strand for each elemental part, and corresponding data stored therein, of each of the plurality of disparate EHRs, each said created data strand labeled with a corresponding FIC and A-I; and
   concatenating, with the computing device, each A-I+FIC-labeled data strand separately for each of the plurality of disparate EHRs.

14. The method of claim 13, wherein the A-I for the data stored in one elemental part of one of the disparate EHRs and the A-I for data stored in another elemental part of the one disparate EHR are the same A-I.

15. The method of claim 12, wherein two or more of the plurality of disparate EHRs comprise distinct electronic data formats.

16. The method of claim 1, further comprising:
   identifying, with a second computing device receiving the concatenated data strands of the source EHR, each data strand for each elemental part of the source EHR from the concatenated data strands;
   identifying, with the second computing device, each elemental part of the source EHR using the FICs in the identified data strands; and
   placing, with the second computing device, each of the identified data strands into corresponding elemental parts of a destination EHR identified using the FICs.

* * * * *